US008822506B2

(12) United States Patent
Labourdette et al.

(10) Patent No.: US 8,822,506 B2
(45) Date of Patent: Sep. 2, 2014

(54) USE OF SUCCINATE DEHYDROGENASE INHIBITORS FOR CONTROLLING POWDERY MILDEW PRIMARY INFECTIONS

(75) Inventors: Gilbert Labourdette, Paray le Monial (FR); Hélène Lachaise, Lyons (FR); Luk de Maeyer, Linter (BE); Christian Feryn, La Roujecie (FR)

(73) Assignee: Bayer Cropscience AG, Monheim (DE)

( * ) Notice: Subject to any disclaimer, the term of this patent is extended or adjusted under 35 U.S.C. 154(b) by 201 days.

(21) Appl. No.: 12/696,776

(22) Filed: Jan. 29, 2010

(65) Prior Publication Data

US 2010/0222397 A1   Sep. 2, 2010

(30) Foreign Application Priority Data

Jan. 30, 2009  (EP) .................................... 09350006

(51) Int. Cl.
*A01N 43/40* (2006.01)
*A01P 3/00* (2006.01)
*A01N 43/56* (2006.01)

(52) U.S. Cl.
CPC ................ *A01N 43/40* (2013.01); *A01N 43/56* (2013.01)
USPC ............................ 514/357; 514/383; 514/406

(58) Field of Classification Search
USPC ......................................... 514/357, 383, 406
See application file for complete search history.

(56) References Cited

U.S. PATENT DOCUMENTS

| | | | |
|---|---|---|---|
| 5,998,450 | A | 12/1999 | Eicken et al. |
| 7,572,818 | B2 | 8/2009 | Mansfield et al. |
| 2004/0204470 | A1 | 10/2004 | Elbe et al. |
| 2006/0116414 | A1 | 6/2006 | Dunkel et al. |
| 2007/0123541 | A1* | 5/2007 | Grosjean-Cournoyer et al. ............ 514/254.07 |
| 2008/0015244 | A1 | 1/2008 | Dunkel et al. |

FOREIGN PATENT DOCUMENTS

| | | |
|---|---|---|
| DE | 19531813 | 10/2003 |
| EP | 07376682 | 10/1996 |
| EP | 1389614 | 2/2004 |
| JP | 2006/213664 A | 8/2006 |
| WO | 2004/016088 | 2/2002 |
| WO | 03010149 | 2/2003 |
| WO | 03070705 | 8/2003 |
| WO | 03074491 | 9/2003 |
| WO | 03074491 A1 | 9/2003 |
| WO | 2004016088 A2 | 2/2004 |
| WO | 2004035589 | 4/2004 |
| WO | 2006015865 | 2/2006 |
| WO | 2006015866 | 2/2006 |
| WO | 2006087343 | 8/2006 |

OTHER PUBLICATIONS

CABA abstract 2007:209574 (2007).*
HCAPLUS abstract 1993:553912 (1993).*
CABA abstract 1996:111857 (1996).*
CABA abstract 1996:86258 (1996).*
Chapman, P.J. et al., "Growth stages in fruit trees—from dormant to fruit set," New York's Food and Life Sciences Bulletin, No. 58, pp. 1-11 (1976).*
Ellis, M., "Apple powdery mildew," The Ohio State University Extension, Fact Sheet, Agriculture and Natural Resources, HYG-3001-08 (2008).*
"Spray Schedule for Apples" publication, Washington State University, Spokane County Extension, Master Gardener Program, p. 1 (Jan. 2005).*
R Birkelt, "Bayer to Boost Agchem R&D Spending," Agrow, XP002535999, Sep. 18, 2008.
C Playsted, "Powdery Mildew Life Cycle and Wine Grape Infection" Queensland Government, XP002536000, Jun. 18, 2007.
B Reinhold Stauss, "Compendium of Growth Stage Identification Keys for Mono-and Dicotyledoneus Plants," BBCH, 1994.
International Search Report of PCT/EP2008/009659; dated Jul. 8, 2009; 2 pgs.

* cited by examiner

*Primary Examiner* — John Pak
(74) *Attorney, Agent, or Firm* — Miles & Stockbridge, P.C.

(57) ABSTRACT

The present invention relates to the use of succinate dehydrogenase Inhibitors for controlling powdery mildew primary infections in crops and to a method for controlling those primary infections.

4 Claims, No Drawings

USE OF SUCCINATE DEHYDROGENASE INHIBITORS FOR CONTROLLING POWDERY MILDEW PRIMARY INFECTIONS

CROSS REFERENCE TO RELATED APPLICATION

This application claims priority to EP 09356006.8 filed Jan. 30, 2009, the content of which is incorporated herein by reference in its entirety.

BACKGROUND

1. Field of the Invention

The present invention relates to the use of succinate dehydrogenase inhibitors for controlling powdery mildew primary infections in crops and to a method for controlling those primary infections.

2. Description of Related Art

Powdery mildew is a fungal disease that affects a wide range of plants. Powdery mildew diseases are caused by many different species of fungi in the order Erysiphales. It is one of the easier diseases to spot, as its symptoms are quite distinctive. Infected plants display white powder-like spots on the leaves and stems and specific russeting on fruits. The younger leaves are the most affected, but the mildew can appear on any part of the plant that shows above the ground. As the disease progresses, the spots get larger and thicker as massive numbers of spores form, and the mildew spreads up and down the length of the plant.

Powdery mildew species over-winter either as mycelium in dormant buds or as cleistothecia on plant tissues. When over-wintering as mycelium in dormant buds, in spring, the shoots arising from the contaminated buds at the end of the previous season become infected and provide inoculum (mycelium and spores) for the subsequent secondary infections and disease development on plant tissues.

It is known in the art that fluopyram shows a high level of efficacy especially against powdery mildew species on different crops. However, powdery mildew can overwinter in buds to produce early infections the year after (primary infected shoots).

Thus, there is a strong need for active ingredients which can be used to reduce the number of primarily infected shoots.

SUMMARY

The problem outlined above has been solved by the use of succinate dehydrogenase inhibitors for controlling powdery mildew primary infections in perennial crops, wherein the succinate dehydrogenase inhibitor was applied to the perennial crop prior to the end of the previous vegetative cycle.

It has surprisingly been found that in the year of the application of the succinate dehydrogenase inhibitor and also in the year after, the number of early infected shoots is significantly reduced and consequently the infection of new growing shoots and leaves is delayed. This finding constitutes a strong advantage for the farmer who can better manage the protection of his orchard.

DETAILED DESCRIPTION OF A PREFERRED EMBODIMENT

In conjunction with the present invention all active substances (a.s.) which inhibit succinate dehydrogenase in the mitochondrial respiration chain can be used. In a preferred embodiment of the present invention the succinate dehydrogenase inhibitor is selected from the group consisting of fluopyram, isopyrazam, boscalid, penthiopyrad, N-[2-(1,3-dimethylbutyl)phenyl]-5-fluoro-1,3-dimethyl-1H-pyrazole-4-carboxamide, sedaxan and bixafen or mixtures thereof. In a most preferred embodiment of the present invention the succinate dehydrogenase inhibitor is fluopyram.

Fluopyram having the chemical name N-{2-[3-chloro-5-(trifluoromethyl)-2-pyridinyl]ethyl}-2-(trifluoromethyl)benzamide is a fungicide belonging to the chemical class of pyridylethylbenzamides. Fluopyram and its manufacturing process starting from known and commercially available compounds is described in EP-A-1 389 614.

Penflufen having the chemical name N-[2-(1,3-dimethylbutyl)phenyl]-5-fluoro-1,3-dimethyl-1H-pyrazole-4-carboxamide and its manufacturing process starting from known and commercially available compounds is described in WO 03/010149.

Bixafen having the chemical name N-(3',4'-dichloro-5-fluoro-1,1'-biphenyl-2-yl)-3-(difluoromethyl)-1-methyl-1H-pyrazole-4-carboxamide (Compound I-2) and its manufacturing process starting from known and commercially available compounds is described in WO 03/070705.

Sedaxane is the mixture of 2 cis-isomers 2'-[(1RS,2RS)-1,1'-bicycloprop-2-yl]-3-(difluoromethyl)-1-methylpyrazole-4-carboxanilide and 2 trans-isomers 2'-[(1RS,2SR)-1,1'-bicycloprop-2-yl]-3-(difluoromethyl)-1-methylpyrazole-4-carboxanilide. Sedaxane and its manufacturing process starting from known and commercially available compounds is described in WO 03/074491, WO 2006/015865 and WO 2006/015866.

Isopyrazam is the mixture of 2 syn-isomers 3-(difluoromethyl)-1-methyl-N—[(1RS,4SR,9RS)-1,2,3,4-tetrahydro-9-isopropyl-1,4-methanonaphthalen-5-yl]pyrazole-4-carboxamide and 2 anti-isomers 3-(difluoromethyl)-1-methyl-N-[(1RS,4SR,9SR)-1,2,3,4-tetrahydro-9-isopropyl-1,4-methanonaphthalen-5-yl]pyrazole-4-carboxamide.
Isopyrazam and its manufacturing process starting from known and commercially available compounds is described in WO 2004/035589.

Penthiopyrad having the chemical name (RS)-N-[2-(1,3-dimethylbutyl)-3-thienyl]-1-methyl-3-(trifluoromethyl)pyrazole-4-carboxamide and its manufacturing process starting from known and commercially available compounds is described in EP-A-0 737 682.

Boscalid having the chemical name 2-chloro-N-(4'-chlorobiphenyl-2-yl)nicotinamide and its manufacturing process starting from known and commercially available compounds is described in DE-A 195 31 813.

Fluxapyraxad having the chemical name 3-(Difluoromethyl)-1-methyl-N-(3',4',5'-trifluorobiphenyl-2-yl)-1H-pyrazole-4-carboxamide and its manufacturing process starting from known and commercially available compounds is described in WO 2006/087343.

In conjunction with the present invention "primary infection" denotes an infection which occurs when water-borne sporangia or zoospores, produced by germinating oospores, are splashed onto wet foliage.

In conjunction with the present invention "controlling" denotes a significant reduction of the powdery mildew infestation in comparison to the untreated crop, more preferably the infestation is essentially diminished (50-79%), most preferably the infestation is totally suppressed (80-100%).

In conjunction with the present invention the time specification "prior to the end of the previous vegetative cycle" means that the succinate dehydrogenase inhibitor, preferably fluopyram was applied to the crop at the previous year at least prior to the abscission of the leaves, preferably prior to the maturation of the fruits for harvesting, most preferably prior to the closing process of the end buds of the extension shoots.

The use/method according to the present invention can be applied to any kind of crops as long as these crops are perennial crops, i.e. plants that live for more than two years. In a preferred embodiment of the invention the crops to be treated are selected from the group consisting of apples, grapes, European gooseberry, chestnut, pecan nuts, cashew, papaya, mango, rambutan, citrus, hazel, pear, cherry, quince, apple, apricot, plum, peach and nectarine. Most preferred are apples and grapes. In a more preferred embodiment of the invention fluopyram is used for controlling powdery mildew infestations in apples or pears.

The succinate dehydrogenase inhibitors, preferably fluopyram can be employed for controlling powdery mildew primary infections within a certain period of time after the treatment. The period of time within which protection is effected generally extends from 1 day to 1 year, preferably from 1 day to 0.5 years after the treatment of the plants with the active compounds. Generally, fluopyram is applied to the trees prior to the end of the previous vegetative cycle.

When employing the succinate dehydrogenase inhibitors, preferably fluopyram, according to the present invention as a fungicide, the application rates can be varied within a broad range, depending on the type of application. For foliar applications the application rates of active compound are generally ranging from 1 to 200 g/ha, more preferably from 10 to 150 g/ha, most preferably from 20 to 50 g/ha based upon the pure a.s. (active substance).

According to the present invention the succinate dehydrogenase inhibitors, preferably fluopyram can be applied to all parts of the plants such as shoot, leaf, flower and root, leaves, needles, stalks, stems, flowers, vegetative buds and flower buds fruiting bodies and fruits.

Plants are understood as meaning, in the present context, all plants and plant populations, such as desired and undesired wild plants or crop plants (including naturally occurring crop plants). Crop plants or crops may be plants which can be obtained by conventional breeding and optimization methods or else by biotechnological and genetic engineering methods or by combinations of these methods, including the transgenic plants and including the plant varieties capable or not capable of being protected by plant breeders' rights.

According to the invention the treatment of the plants with the succinate dehydrogenase inhibitors, preferably fluopyram is carried out directly by the customary treatment methods, for example by immersion, spraying, vaporizing, fogging, injecting, dripping, drenching, broadcasting or painting. In a preferred embodiment of the invention fluopyram is applied by injecting, dripping, drenching or spraying.

The succinate dehydrogenase inhibitors, preferably fluopyram can be converted to the customary formulations, such as solutions, emulsions, suspensions, powders, foams, pastes, granules, aerosols, very fine capsules in polymeric substances and in coating compositions for seed, and also ULV cold- and warm-fogging formulations.

These formulations are produced in a known manner, for example by mixing the active compounds with extenders, that is liquid solvents, pressurized liquefied gases and/or solid carriers, optionally with the use of surface-active agents, that is emulsifiers and/or dispersants and/or foam formers. If the extender used is water, it is also possible to employ for example organic solvents as cosolvents. Suitable liquid solvents are essentially: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water. Liquefied gaseous extenders or carriers are those liquids which are gaseous at ambient temperature and at atmospheric pressure, for example aerosol propellants such as halogenated hydrocarbons and also butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates. As solid carriers for granules there are suitable: for example crushed and fractionated natural rocks such as calcite, pumice, marble, sepiolite and dolomite, and also synthetic granules of inorganic and organic meals, and granules of organic material such as sawdust, coconut shells, maize cobs and tobacco stalks. As emulsifiers and/or foam formers there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and protein hydrolysates. As dispersants, for example, lignosulphite waste liquors and methylcellulose are suitable.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other possible additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compounds, preferably between 0.5 and 90 percent by weight, based upon the total formulation.

According to the present invention, the succinate dehydrogenase inhibitors, preferably fluopyram as such or their formulations, can also be used as a mixture with known fungicides, bactericides, acaricides, nematicides, or insecticides, for example, to broaden the activity spectrum or prevent the development of resistance. In many instances, synergistic effects are obtained, i.e. the activity of the mixture exceeds the activity of the individual components.

A further embodiment of the invention relates to the use of a composition comprising a succinate dehydrogenase inhibitor, preferably fluopyram and a second fungicide for controlling powdery mildew primary infections in perennial crops.

Suitable fungicides which can be used in combination with the succinate dehydrogenase inhibitor, preferably with fluopyram are selected from the group consisting of (1) Inhibitors of the nucleic acid synthesis, for example benalaxyl, benalaxyl-M, bupirimate, clozylacon, dimethirimol, ethirimol, furalaxyl, hymexazol, metalaxyl, metalaxyl-M, ofurace, oxadixyl and oxolinic acid.

(2) Inhibitors of the mitosis and cell division, for example benomyl, carbendazim, chlorfenazole, diethofencarb, ethaboxam, fuberidazole, pencycuron, thiabendazole, thiophanate, thiophanate-methyl and zoxamide.

(3) Inhibitors of the respiration, for example diflumetorim as CI-respiration inhibitor; bixafen, boscalid, carboxin, fenfuram, flutolanil, fluopyram, furametpyr, furmecyclox, isopyrazam (9R-component), isopyrazam (9S-component), mepronil, oxycarboxin, penthiopyrad, thifluzamide as CII-respiration inhibitor; amisulbrom, azoxystrobin, cyazofamid, dimoxystrobin, enestroburin, famoxadone, fenamidone, fluoxastrobin, kresoxim-methyl, metominostrobin, orysastrobin, picoxystrobin, pyraclostrobin, pyribencarb, trifloxystrobin as CIII-respiration inhibitor.
(4) Compounds capable to act as an uncoupler, like for example binapacryl, dinocap, fluazinam and meptyldinocap.
(5) Inhibitors of the ATP production, for example fentin acetate, fentin chloride, fentin hydroxide, and silthiofam.
(6) Inhibitors of the amino acid and/or protein biosynthesis, for example andoprim, blasticidin-S, cyprodinil, kasugamycin, kasugamycin hydrochloride hydrate, mepanipyrim and pyrimethanil.
(7) Inhibitors of the signal transduction, for example fenpiclonil, fludioxonil and quinoxyfen.
(8) Inhibitors of the lipid and membrane synthesis, for example biphenyl, chlozolinate, edifenphos, etridiazole, iodocarb, iprobenfos, iprodione, isoprothiolane, procymidone, propamocarb, propamocarb hydrochloride, pyrazophos, tolclofos-methyl and vinclozolin.
(9) Inhibitors of the ergosterol biosynthesis, for example aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, viniconazole and voriconazole.
(10) Inhibitors of the cell wall synthesis, for example benthiavalicarb, dimethomorph, flumorph, iprovalicarb, mandipropamid, polyoxins, polyoxorim, prothiocarb, validamycin A, and valiphenal.
(11) Inhibitors of the melanine biosynthesis, for example carpropamid, diclocymet, fenoxanil, phthalide, pyroquilon and tricyclazole.
(12) Compounds capable to induce a host defence, like for example acibenzolar-5-methyl, probenazole, and tiadinil.
(13) Compounds capable to have a multisite action, like for example bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxine-copper, propamidine, propineb, sulphur and sulphur preparations including calcium polysulphide, thiram, tolylfluanid, zineb and ziram.
(14) Further compounds like for example 2,3-dibutyl-6-chlorothieno[2,3-d]pyrimidin-4(3H)-one, ethyl (2Z)-3-amino-2-cyano-3-phenylprop-2-enoate, N-[2-(1,3-dimethylbutyl)phenyl]-5-fluoro-1,3-dimethyl-1H-pyrazole-4-carboxamide, N-{2-[1,1'-bi(cyclopropyl)-2-yl]phenyl}-3-(difluoromethyl)-1-methyl-1H-pyrazole-4-carboxamide, 3-(difluoromethyl)-1-methyl-N-(3',4',5'-trifluorobiphenyl-2-yl)-1H-pyrazole-4-carboxamide, 3-(difluoromethyl)-N-[4-fluoro-2-(1,1,2,3,3,3-hexafluoropropoxy)phenyl]-1-methyl-1H-pyrazole-4-carboxamide, (2E)-2-(2-{[6-(3-chloro-2-methylphenoxy)-5-fluoropyrimidin-4-yl]oxy}phenyl)-2-(methoxyimino)-N-methylethanamide, (2E)-2-{2-[({[(2E,3E)-4-(2,6-dichlorophenyl)but-3-en-2-ylidene]amino}oxy)methyl]phenyl}-2-(methoxyimino)-N-methylethanamide, 2-chloro-N-(1,1,3-trimethyl-2,3-dihydro-1H-inden-4-yl)pyridine-3-carboxamide, N-(3-ethyl-3,5,5-trimethylcyclohexyl)-3-(formyl-amino)-2-hydroxybenzamide, 5-methoxy-2-methyl-4-(2-{[({(1E)-1-[3-(trifluoromethyl)-phenyl]ethylidene}amino)oxy]methyl}phenyl)-2,4-dihydro-3H-1,2,4-triazol-3-one, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}-imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N-ethyl-N-methyl-N'-{2-methyl-5-(trifluoromethyl)-4-[3-(trimethylsilyl)propoxy]phenyl}-imidoformamide, N'-{5-(difluoromethyl)-2-methyl-4-[3-(trimethylsilyl)propoxy]phenyl}-N-ethyl-N-methylimidoformamide, O-{1-[(4-methoxyphenoxy)methyl]-2,2-dimethylpropyl} 1H-imidazole-1-carbothioate, N-[2-(4-{[3-(4-chlorophenyl)prop-2-yn-1-yl]oxy}-3-methoxyphenyl)ethyl]-N$^2$-(methylsulfonyl)valinamide, 5-chloro-7-(4-methylpiperidin-1-yl)-6-(2,4,6-trifluorophenyl)[1,2,4]triazolo[1,5-a]pyrimidine, 5-amino-1,3,4-thiadiazole-2-thiol, propamocarb-fosetyl, 1-[(4-methoxyphenoxy)methyl]-2,2-dimethylpropyl 1H-imidazole-1-carboxylate, 1-methyl-N-[2-(1,1,2,2-tetrafluoroethoxy)phenyl]-3-(trifluoromethyl)-1H-pyrazole-4-carboxamide, 2,3,5,6-tetrachloro-4-(methylsulfonyl)pyridine, 2-butoxy-6-iodo-3-propyl-4H-chromen-4-one, 2-phenylphenol and salts, 3-(difluoromethyl)-1-methyl-N-[2-(1,1,2,2-tetrafluoroethoxy)phenyl]-1H-pyrazole-4-carboxamide, 3,4,5-trichloropyridine-2,6-dicarbonitrile, 3-[5-(4-chlorophenyl)-2,3-dimethylisoxazolidin-3-yl]pyridine, 3-chloro-5-(4-chlorophenyl)-4-(2,6-difluorophenyl)-6-methylpyridazine, 4-(4-chlorophenyl)-5-(2,6-difluorophenyl)-3,6-dimethylpyridazine, quinolin-8-ol, quinolin-8-ol sulfate (2:1) (salt), 5-methyl-6-octyl-3,7-dihydro[1,2,4]triazolo[1,5-a]pyrimidin-7-amine, 5-ethyl-6-octyl-3,7-dihydro[1,2,4]triazolo[1,5-a]pyrimidin-7-amine, benthiazole, bethoxazin, capsimycin, carvone, chinomethionat, chloroneb, cufraneb, cyflufenamid, cymoxanil, cyprosulfamide, dazomet, debacarb, dichlorophen, diclomezine, dicloran, difenzoquat, difenzoquat methylsulphate, diphenylamine, ecomate, ferimzone, flumetover, fluopicolide, fluoroimide, flusulfamide, flutianil, fosetyl-aluminium, fosetyl-calcium, fosetyl-sodium, hexachlorobenzene, irumamycin, isotianil, methasulfocarb, methyl (2E)-2-{2-[({cyclopropyl[(4-methoxyphenyl)imino]methyl}thio)methyl]phenyl}-3-methoxyacrylate, methyl isothiocyanate, metrafenone, (5-bromo-2-methoxy-4-methylpyridin-3-yl)(2,3,4-trimethoxy-6-methylphenyl)methanone, mildiomycin, tolnifanide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-bromo-3-chloropyridin-2-yl)methyl]-2,4-dichloropyridine-3-carboxamide, N-[1-(5-bromo-3-chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(Z)-[(cyclopropylmethoxy)imino][6-(difluoromethoxy)-2,3-difluorophenyl]methyl}-2-phenylacetamide, N-{(E)-[(cyclopropylmethoxy)imino][6-(difluoromethoxy)-2,3-difluorophenyl]methyl}-2-phenylacetamide, natamycin, nickel dimethyldithiocarbamate, nitrothal-isopropyl, octhilinone, oxamocarb, oxyfenthiin, pentachlorophenol and salts, phenazine-1-carboxylic acid, phenothrin, phosphorous acid and its salts, propamocarb fosetylate, propanosine-sodium, proquinazid, pyrrolnitrine, quintozene, S-prop-2-en-1-yl 5-amino-2-(1-methylethyl)-4-(2-methylphenyl)-3-oxo-2,3-dihydro-1H-pyrazole-1-carbothioate, tecloftalam, tecnazene, triazoxide, trichlamide, 5-chloro-N'-phenyl-N'-prop-2-yn-1-ylthiophene-2-sulfonohydrazide and zarilamid. In a preferred embodiment the second fungicide is tebuconazole. In a more preferred embodiment of the invention a composition comprising fluopyram and tebuconazol is used for controlling powdery mildew infestations in apples or pears.

A further embodiment of the present invention is a method for controlling powdery mildew primary infections of crops, preferably *Podosphera leucotricha* of apple trees, characterized in that, fluopyram was applied to the perennial crop prior to the end of the previous vegetative cycle.

The present invention is exemplified by the following examples.

EXAMPLES

Fluopyram was tested in apples orchard in comparison with already know fungicides active against Powdery mildew such as triadimenol (Bayleton) and boscalid.

Fluopyram was applied at range of rates: 18.5 g-25 g-37.5-50 g a.s./ha/meter canopy height (g ha/m c.h.). Bayleton was applied at 25 g a.s./ha/m c.h. Boscalid (Cantus WG50) was applied at 125 g a.s./m c.h.

Trial Conditions

During the spray season, the compounds were applied at apple susceptible stages from BBCH09 (green leaf tips 5 mm above bud scales to BBCH73 Fruit size between 20 and 40 mm (as described in BBCH Monograph, 2. Edition, 2001, edited by Uwe Meier, Federal Biological Research Centre for Agriculture and Forestry) in order to protect leaves, buds and shoots against Powdery mildew. The compounds have been applied eight times with an interval of ten days during spray season.

Assessment

The type of assessments of infections was:

% infested area on leaves (severity) and % infested leaves (incidence) were assessed 10 days after application 8 (10DAT8).

Count and % infested shoots (primary infection) were assessed 345 days after application 8 (345 DAT8).

Results

TABLE 1

| Compounds/g a.s./ha/m c.h. | 10DAT8 [% infested leaves] | 10DAT8 [% efficacy] (Abbott)*[1] | 345DAT8 [% infested shoots] | 345DAT8 [% efficacy] (Abbott)*[1] |
| --- | --- | --- | --- | --- |
| Untreated | 96 | | 45.2 | |
| Triadimenol @ 25 g | 32 | 66.7 | 27.5 | 39.1 |
| Fluopyram @ 18.5 g | 8.7 | 91 | 17.7 | 60.9 |
| Fluopyram @ 25 g | 10 | 89.6 | 14 | 69 |
| Fluopyram @ 37.5 g | 2.7 | 97.2 | 13 | 71.2 |
| Fluopyram @ 50 g | 0.7 | 99.3 | 9 | 80.1 |
| Boscalid @ 125 g | 46 | 52.1 | 30.8 | 31.7 |

*[1]Abbott, W.S. (1925). J. Econ. Entomol.; 18: 265-267.

As it becomes evident from the above table 1, fluopyram clearly demonstrate an excellent efficacy against powdery mildew on apples against secondary infections controlled during the spray program (assessment 10DAT8), with a visible dose rate effect between 18.5 g to 50 g a.s./m c.h. This efficacy, from the lowest rate is superior to triadimenol (25 g a.s./m c.h) and boscalid (125 g a.s./m c.h.).

In the proximate year (assessment 365DAT8), without any other application, the level of infection measured by the % of primary infested shoots shows clearly a high decrease of infestation in fluopyram treated plots with a dose rate relation. Significant protection, superior to triazoles and other SDH inhibitors, is achieved with 50 g a.s./m c.h but already superior at 18.5 g g a.s./m.c.h.

The invention claimed is:

1. A method for controlling powdery mildew primary infections in an apple crop comprising applying fluopyram to the apple crop prior to the end of a vegetative cycle,
    wherein the fluopyram is applied to the apple crop prior to abscission of leaves, and
    wherein the powdery mildew primary infections are controlled for a year after application of the fluopyram,
    wherein the fluopyram is applied at a rate ranging from 18.5 to 50 g a.s./ha/m c.h.

2. The method according to claim 1, wherein the fluopyram is applied to the apple crop prior to maturation of fruits for harvesting.

3. The method according to claim 1, wherein the fluopyram is applied to the apple crop prior to a closing process of end buds of extension shoots.

4. A method according to claim 1, wherein the fluopyram is applied to control *Podosphera leucotricha* in an apple crop.

\* \* \* \* \*